United States Patent
Chen et al.

(10) Patent No.: US 11,389,382 B2
(45) Date of Patent: Jul. 19, 2022

(54) BIPHASE CHEMICAL PEEL

(71) Applicant: L'OREAL, Paris (FR)

(72) Inventors: Rebecca Chen, Princeton, NJ (US); Seung Ook Yang, Kawasaki (JP); Anne-Laure Suzanne Bernard, New York, NY (US)

(73) Assignee: L'OREAL, Paris (FR)

( * ) Notice: Subject to any disclaimer, the term of this patent is extended or adjusted under 35 U.S.C. 154(b) by 37 days.

(21) Appl. No.: 16/583,451

(22) Filed: Sep. 26, 2019

(65) Prior Publication Data

US 2021/0093530 A1    Apr. 1, 2021

(51) Int. Cl.
| | |
|---|---|
| *A61K 8/37* | (2006.01) |
| *A61K 8/34* | (2006.01) |
| *A61K 8/365* | (2006.01) |
| *A61Q 19/00* | (2006.01) |

(52) U.S. Cl.
CPC ............... *A61K 8/37* (2013.01); *A61K 8/347* (2013.01); *A61K 8/365* (2013.01); *A61Q 19/00* (2013.01); *A61K 2800/33* (2013.01); *A61K 2800/75* (2013.01)

(58) Field of Classification Search
None
See application file for complete search history.

(56) References Cited

U.S. PATENT DOCUMENTS

| | | | |
|---|---|---|---|
| 4,608,370 A | 8/1986 | Aronsohn | |
| 2009/0137534 A1* | 5/2009 | Chaudhuri | ........... A61K 31/203 |
| | | | 514/159 |
| 2016/0374912 A1 | 12/2016 | Lu et al. | |
| 2017/0182069 A1* | 6/2017 | Lu | ........................ A61K 8/347 |

FOREIGN PATENT DOCUMENTS

CN        1100528 C    2/2003

OTHER PUBLICATIONS

Genius Ultimate Anti-Aging Bi-Phase Peel, https://www.beautypedia.com/products/genius-ultimate-anti-aging-bi-phase-peel/ (Jul. 7, 2017). (Year: 2017).*
Mintel, Algenist, "Ultimate Anti-Aging Bi-Phase Peel" https://www.algenist.com/products/genius-ultimate-anti-aging-bi-phase-peel/, Record ID 3108161, (May 2015).
Mintel, "Biphasic Make Up Remover," https://gnpd.com, Record ID 6491349, XP055755998, (First page only) (Apr. 2019).
(Continued)

*Primary Examiner* — Bethany P Barham
*Assistant Examiner* — Barbara S Frazier
(74) *Attorney, Agent, or Firm* — McNees Wallace & Nurick LLC

(57) ABSTRACT

A biphasic leave-on skin peel composition, being lightweight, with a pleasing feel upon application, with little to no skin irritation and discomfort. The composition includes at least one of each of alpha and beta hydroxy acids and high content of non-water miscible oil and is present from at least 20% by weight based on the total weight of the composition. The oily and water phases may be present in equal amounts (about 1:1). The composition includes water and alcohol as solvents in the water phase and may include phenylethyl resorcinol and other optional additives, may be devoid or essentially free of surfactant.

20 Claims, 2 Drawing Sheets

(56) References Cited

OTHER PUBLICATIONS

Mintel, "Light Peel Daily Glow Activator Resurfacing Lotion" https://gnpd.com, Record ID 5928581, XP055756002, (Aug. 2018).
PCT Notification of Transmittal of the International Search Report and the Written Opinion of the International Searching Authority, or the Declaration, issued to PCT/US2020/052798 dated Dec. 14, 2020.

* cited by examiner

BIPHASE CHEMICAL PEEL

FIELD OF THE INVENTION

The invention relates to a biphase, leave-on, skin peel that is gentle and non-greasy with high desquamation efficacy.

BACKGROUND OF THE INVENTION

Chemical peels are a non-invasive dermatological treatment techniques to improve and treat skin conditions including: photodamaged skin, hyperpigmentation, acne vulgaris, rosacea, premalignant skin cancer, wrinkles and fine lines, superficial scars and the like. These cosmetic compositions include a solution of acids that, when applied topically, penetrate into the skin, inducing and accelerating skin's natural regeneration process by sloughing off dead top layers of skin. The strength and efficacy of a peel is dictated by the formulation, acid type and concentration, which factors affect depth of penetration into the skin. Common chemical peels compositions include one or more of glycolic acid, lactic acid, salicylic acid, and trichloroacetic acid (TCA), among other ingredients. Peels with high levels of acid (greater than 30%) and extreme low pH (less than 3) are considered professional use are typically limited to use with licensed dermatologists and/or aestheticians.

Peels that are used in the home market typically include a total alpha hydroxy acid (glycolic, lactic acid, mandelic acid, etc.) at a concentration of less than 10%, with a final pH that is greater than 3.0. A specific example of peel compositions includes Jessner peels (Salicylic+Lactic+Resorcinol) which are provided with professional levels of acids, as well as lower amounts of acids suitable for home use, are popular and considered efficacious. The home use versions of these peels demonstrate moderate clinical efficacy as compared with professional-type compositions and are considered safe enough for self-application at home with minimal risk of acid-related burns. The challenge with home peels lies in delivering clinical-like efficacy with the lower acid level and elevated formulation pH. Better skin rejuvenation/desquamation efficacy of chemical peels can be achieved by increasing the acid concentration and combining alpha- and beta-hydroxyl acids. However, with the increased concentration of organic acid, the discomfort level significantly increases as well. In this invention the immiscible oil can enrich the actives (AHA and BHA) in the aqueous phase, therefore enhance the desquamation efficacy without increasing discomfort level Therefore, a need exists for a chemical skin peeling composition that provides exceptional results, without or with less adverse side effects or drawbacks found with conventional chemical peels.

The biphase, leave-on peel composition according to the instant disclosure provides a high desquamation efficacy with minimal discomfort.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

In various embodiments, provided is a biphasic leave-on skin peel composition, being light-weight, with a pleasing feel upon application, with little to no skin irritation and discomfort. The composition includes at least one of each of alpha and beta hydroxy acids and high content of non-water miscible oil and is present from at least 20% by weight based on the total weight of the composition. The oily and water phases may be present in equal amounts (about 1:1). The composition includes water and alcohol as solvents in the water phase and may include phenylethyl resorcinol and other optional additives and may be devoid or essentially free of surfactant.

In accordance with the various embodiments, provided is a biphasic skin peel composition that includes at least one of each of alpha and beta hydroxy acids, and at least one non-water miscible oil present from at least 20% by weight based on the total weight of the composition. The alpha and beta hydroxy acids, water and alcohol are present in a water phase, and the non-water miscible oil is present in an oily phase, and wherein the water and oily phases are present in equal amounts (about 1:1).

In some embodiments, the biphasic skin peel includes phenylethyl resorcinol. In some embodiments, composition further includes from about 0.2% to about 0.8%, by weight, of phenylethyl resorcinol.

In some embodiments, the alpha hydroxy acid includes one or more of lactic acid and glycolic acid, the beta hydroxy acid includes salicylic acid, and the non-water miscible oil is selected from the group consisting of isopropyl myristate, isononyl isononanoate, dicaprylyl carbonate, mineral oil, C13-15 alkane/hemisqualane, squalane, dimethicone, C17-18 branched alkanes, and combinations thereof.

In some embodiments, the composition is surfactant free.

In some embodiments, the alpha hydroxy acid is selected from the group consisting of lactic acid, glycolic acid, tartaric acid, mandelic acid, citric acid, ester derivatives thereof and combinations thereof. In some embodiments, the composition includes from about 4% to about 15%, by weight, of alpha hydroxy acid. In some embodiments, the composition includes about 10.0%, by weight, of alpha hydroxy acid. In some embodiments, the alpha hydroxy acid is lactic acid.

In some embodiments, the composition includes from about 0.2% to about 2%, by weight, of salicylic acid. In some embodiments, the composition includes about 0.45%, by weight, of salicylic acid.

In some embodiments, the composition further includes from about 5% to about 20%, by weight, of alcohol.

In some embodiments, the at least one non-water miscible oil is present an oily phase, the oil present in an amount from at least about 20% and up to about 60%, and wherein water and each of the at least one at least alpha hydroxy acid and beta hydroxy acid is present in a water phase, wherein the water phase is present in an amount from about 40% to about 80%, all percentages by weight, based on the total weight of the composition.

In some embodiments, the biphasic skin peel composition includes one or more additives selected from citric acid, sodium chloride; chelating agents; antimicrobial agents; neutralizing/pH-adjusting agents; vitamins; fragrances; pearlescent agents; odor absorbers; coloring materials; essential oils; fruit extracts; and combinations thereof.

In some particular embodiments, provided is a biphasic skin peel composition that includes at least alpha hydroxy acid present from about 8% to about 12%, by weight, based on the total weight of the composition; at least beta hydroxy acid present from about 0.35% to about 0.75%, by weight, based on the total weight of the composition; at least one non-water miscible oil present from at least about 20% by weight based on the total weight of the composition; phenylethyl resorcinol present from about 0.7% to about 0.8%, by weight, based on the total weight of the composition.

In accordance with some such embodiments, the at least one alpha hydroxy acid includes lactic acid; the at least one beta hydroxy acid includes salicylic acid; the at least one non-water miscible oil is selected from the group consisting of isopropyl myristate, isononyl isononanoate, dicaprylyl carbonate, mineral oil, C13-15 alkane/hemisqualane, squalane, dimethicone, C17-18 branched alkanes, and combinations thereof.

In accordance with some such embodiments, the composition is surfactant free. In accordance with some such embodiments, the at least one non-water miscible oil is present an oily phase, and wherein water and each of the at least one at least alpha hydroxy acid and beta hydroxy acid is present in a water phase, wherein the water phase is present in an amount from about 40% to about 80%, all percentages by weight, based on the total weight of the composition.

Other features and advantages of the present invention will be apparent from the following more detailed description, by way of example, the principles of the invention.

This disclosure describes particular embodiments in accordance with the general inventive concepts and is not intended to limit the scope of the invention in any way. Indeed, the invention as described in the specification is broader than and unlimited by the particular embodiments set forth herein, and the terms used herein have their full ordinary meaning.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

Figure 1:
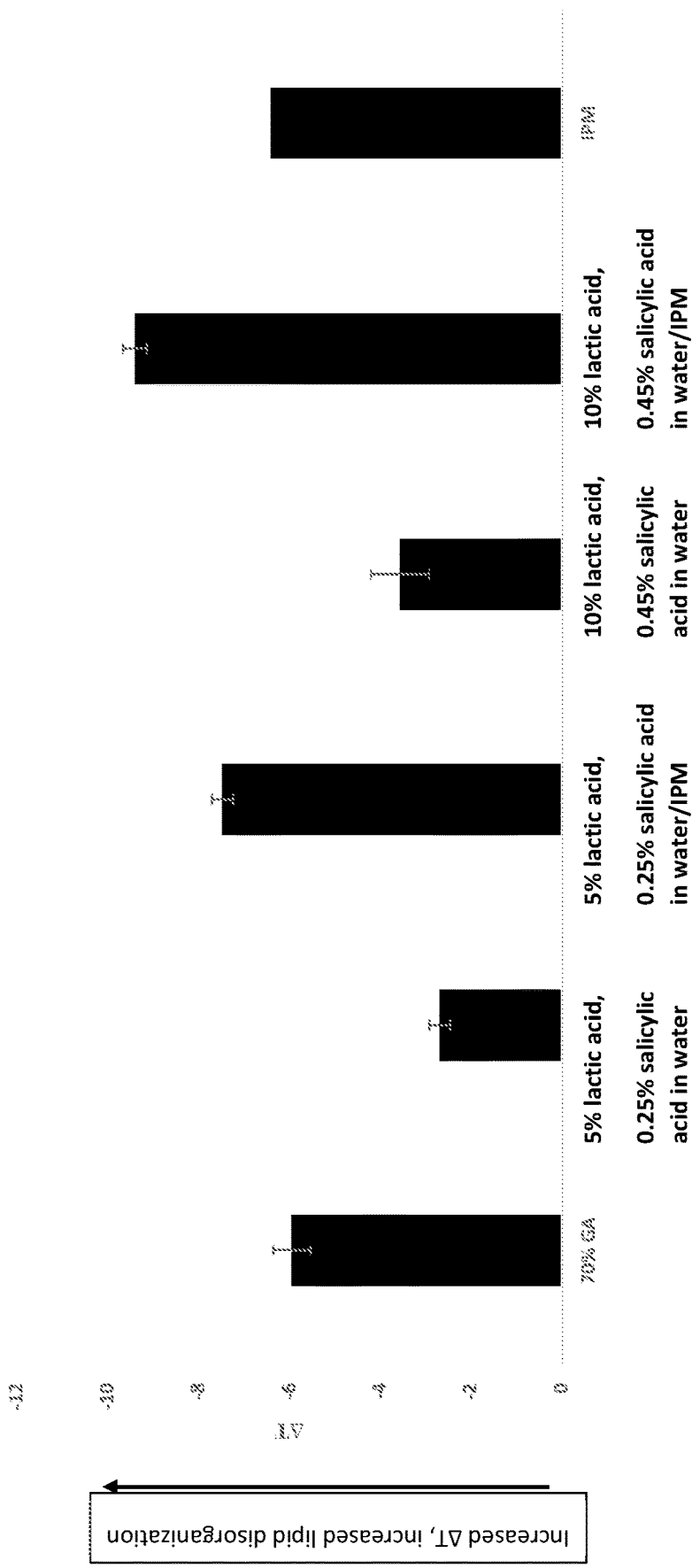
FIG. 1 is a bar graph showing comparative performance results demonstrating lipid disorganization.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

"Keratinous substrate" and "keratinous tissue" each includes but is not limited to skin, scalp, hair, and nails.

The term "surfactant free" as used herein means that excluded surfactants have not been added as a component. In some embodiments, a composition is devoid of surfactants. Those of skill in the art will appreciate that a surfactant may be present in a composition via its presence in one or more of the formulation components; thus, in some embodiments a composition may be "essentially surfactant-free" wherein surfactant is present at a concentration that does not exceed 5% by weight, and in some instances is present not more than 3% by weight, and in some instances is present not more than 1% by weight, based on the weight of the composition. In some particular embodiments "surfactant-free" means that the composition is free or devoid specifically of surfactant. Some specific but non-limiting examples of surfactants that are lacking from the composition includes those with a C10-C20 fatty alcohol or acid hydrophobe condensed with from about 2 to about 100 moles of ethylene oxide or propylene oxide per mole of hydrophobe; C2-C10 alkyl phenols condensed with from 2 to 20 moles of alkylene oxide; mono- and di-fatty acid esters of ethylene glycol; fatty acid monoglyceride; sorbitan; mono- and di-C8-C20 fatty acids; polyoxyethylene sorbitan; alkyl polyglycosides and saccharide fatty amides (e.g. methyl gluconamides); alkyl ether sulfate and sulfonates; alkyl sulfates and sulfonates; alkylbenzene sulfonates; alkyl and dialkyl sulfosuccinates; C8-C20 acyl isethionates; C8-C20 alkyl ether phosphates; alkylethercarboxylate. Some specific surfactants that are lacking from the composition include PEG-100 Stearate; PEG-20 Stearate and other esters of Poly(Ethylene Glycol); Sucrose Stearate and other emulsifiers based on sugar esters; Glyceryl Stearate and other glycerol esters; Disodium Ethylene Dicocamide PEG-15 Disulfate; Sodium Steroyl Glutamate and other fatty amides; Steareth-100 and other fatty ethers; Acrylates/C10-30 Alkyl Acrylate Crosspolymer and similar polymeric emulsifiers.

In accordance with the various embodiments, the composition is a biphase, composition, that is, at least in some embodiments, free or essentially free of surfactant. In some particular embodiments, the composition is devoid of surfactants. In some embodiments, the composition is used on one or more of the parts of or the entire body, the face, the hair and/or scalp, and discrete body parts.

The composition according to the instant disclosure provides a biphase leave on product, in some embodiments, without surfactants, that includes high concentration >20% and up to about 60% of oil in combination with alpha and beta hydroxy acids. The composition is shaken or agitated to form an emulsion just prior to application. The composition is light-weight, much like a toner, with a pleasing feel upon application, and is convenient in that it does not need to be removed. And the composition advantageously delivers peeling efficacy with unexpectedly little to no skin irritation and discomfort. Moreover, the composition provides significantly enhanced efficacy, even at one half the amount of acid, as compared with commercially available chemical peel formulations that lack oil.

As shown in the Examples, the inventive composition demonstrates the same or improved desquamation efficacy as compared to the conventional, at home and mild Jessner type peels. Further unexpected benefits include user comfort even at higher levels of acid. Efficacy results are shown by measurement of lipid disorganization in stratum corneum samples and in measurement of protein removal in skin strip removal assays.

In various embodiments, the biphasic composition is a skin peel that may be left on after application, or optionally removed by the user, and includes at least one of each of alpha and beta hydroxy acids and high content of non-water miscible oil present from at least 20% by weight based on the total weight of the composition. In some embodiments the oily and water phases are present in equal amounts (about 1:1). In various embodiments, the inventive composition includes water and alcohol as solvents in the water phase and may include phenylethyl resorcinol and other optional additives.

Biphasic Composition

The composition according to the disclosure is a two-phase, or biphasic cosmetic composition that consist of two distinct phases, an aqueous phase and an oily phase, which are easily emulsified by stirring and which rapidly separate/ phase out at rest. The use of this type of biphasic composition involves pre-application agitation to form an emulsion prior to application to the keratinous tissue, such as skin, which emulsion is of sufficient quality and stability to allow a uniform application of the emulsified phases. In some embodiments, the oily phase comprising at least one oil is present in an amount that is present from at least about 20% and up to about 50% or about 60%, and the water phase comprising water and water miscible components which include the acids including alcohol solvent, and phenylethyl resorcinol and any additives, when present, is present in an amount from about 40% to about 80%, all percentages by weight, based on the total weight of the composition. In some embodiments, the oily and water phases are present in a ratio of about 1:1.

Oil

In accordance with the various embodiments, the composition according to the disclosure comprises at least one non water-miscible oil.

In the various embodiments, the at least one oil is generally immiscible in water, and may be selected from hydrocarbons, silicones, fatty alcohols, glycols and vegetable oils. The at least one oil may include one or a combination of polar and non-polar oil. In some embodiments, the oil may be chosen from hydrocarbon-based oils from plants or of plant origin, mineral oil, ester oils, fatty alcohols containing from 12 to 26 carbon atoms, fatty acids containing from 12 to 26 carbon atoms and vinylpyrrolidone copolymers, and mixtures thereof. In some particular embodiments, an oil may be chosen from purcellin oil (cetostearyl octanoate), squalane, hemisqualane, isononyl isononanoate, C12 to C15 alkyl benzoate, 2-ethylhexyl palmitate, isodecyl neopentanoate, tridecyl neopentanoate, octyldodecyl neopentanoate, 2-octyldodecyl stearate, 2-octyldodecyl erucate, oleyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate and 2-diethylhexyl succinate, cocoglyceride, cyclomethicone, dimethicone, dicaprylyl carbonate, dicapryl maleate, caprylic/capric triglyceride, isopropyl myristate, octyl stearate, isostearyl linoleate, lanolin oil, coconut oil, cocoa butter, olive oil, avocado oil, aloe extracts, jojoba oil, castor oil, fatty acid, oleic acid, stearic acid, fatty alcohol, cetyl alcohol, hexadecyl alcohol, diisopropyl adipate, hydroxybenzoate esters, benzoic acid esters of C9-C15 alcohols, alkanes, mineral oil, silicone, dimethyl polysiloxane, ether, polyoxypropylene butyl ether, polyoxypropylene cetyl ether, C12-C15 alkyl benzoate, aryl alkyl benzoate, Isopropyl Lauroyl sarcosinate, and any combinations thereof.

In some particular embodiments, the oil is chosen from C13-15 alkane (hemisqualane), dicaprylyl carbonate, isononyl isononanoate, isopropyl myristate, dimethicone, squalane, and mineral oil. In an exemplary embodiment, the oil comprises one or a combination of C13-15 alkane (hemisqualane), dicaprylyl carbonate, isononyl isononanoate, isopropyl myristate, dimethicone, squalane, and mineral oil. In some embodiments, the oil in the composition includes isopropyl myristate.

In accordance with the various embodiments, the amount of at least one oil present in the composition is at least about 20%, and can range from about 20% to about 60%, or from about 25% to about 55%, or from about 30% to about 50%, or any suitable combination, sub-combination, range, or sub-range thereof by weight, based on the weight of the composition. One of ordinary skill in the art, however, will appreciate that other ranges are within the scope of the invention. The composition may include more than one oil, such as a mixture of oils wherein one or the mixture of oils is present in an amount that alone, or combined is at least 20% by weight based on the weight of the composition, and wherein the total amount of oil is present up to about 60% of the composition.

Thus, any one of or a combination of oils may be present, by weight, based on the total weight of the composition, from about at least 20, 21, 22, 23, 24, 25, 26, 27, 28, 29, 31, 31, 32, 33, 34, 35, 36, 37, 38, 39, 40, 41, 42, 43, 44, 45, 46, 47, 48, 49, 50, 51, 52, 53, 54, 55, 56, 57, 58, 59 to about 60 weight percent, including increments and ranges therein and there between.

Acids

Alpha Hydroxy Acid

In accordance with the various embodiments, the composition according to the disclosure comprises at least one alpha hydroxy acid.

Suitable alpha hydroxy acids include lactic acid, glycolic acid, tartaric acid, mandelic acid, citric acid, ester derivatives thereof and combinations thereof. Exemplary ester derivatives include ester compounds of lactic acid, such as methyl lactate, ethyl lactate, butyl lactate and, similarly, ester compounds of glycolic acid, tartaric acid, mandelic acid, citric acid. One particularly suitable alpha hydroxy acid is lactic acid. Lactic acid, or 2-hydroxypropanoic acid, is provided to the chemical peel composition to provide enhanced exfoliation of the skin. In addition, lactic acid also boosts production of glycosaminoglycan (GAG) in the skin, improving the barrier function and moisturization of skin. In some embodiments, the composition includes one or both lactic acid and glycolic acid, and in some particular embodiments, the alpha hydroxy acid in the composition consists of lactic acid.

The composition, according to the present disclosure, includes a concentration of alpha hydroxy acid, said composition being characterized in that it has a concentration of alpha hydroxy acid in a range from about 4% to about 15%, or from about 8% to about 14% or from about 9% to about 13%, or from about 10% to about 12%, or is about 10%, or any suitable combination, sub-combination, range, or sub-range thereof by weight, based on the weight of the composition. In accordance with some embodiments, the amount of alpha hydroxy acid present is not more than about 10%.

Thus, any one of or a combination of alpha hydroxy acid is present, by weight, based on the total weight of the composition, from about 4, 5, 6, 7, 8, 9, 10, 11, 12, 13, 14, to about 15 weight percent, including increments and ranges therein and there between.

Beta Hydroxy Acid

In accordance with the various embodiments, the composition according to the disclosure comprises at least one beta hydroxy acid.

Suitable beta hydroxy acids are selected from salicylic acid, beta-hydroxypropionic acid, beta-hydroybutyric acid, beta-hydroxy beata-methylbutyric acid, carnitine, and combinations of these.

In some particular embodiments, the composition, according to the present disclosure, includes salicylic acid. Salicylic acid, or 2-hydroxybenzoic acid, is provided to the chemical peel composition to provide enhanced penetration of the composition into the skin. Salicylic acid penetrates deeper into the skin than alpha hydroxy acids, such as lactic acid. Salicylic acids is an effective keratolytic and comedolytic agent, inducing desquamation and can be used to effectively treat excessive oil, acne, post-inflammatory hyperpigmentation, and photodamage.

The composition, according to the present disclosure, includes a concentration of beta hydroxy acid, said composition being characterized in that it has a concentration of beta hydroxy acid in a range from about 0.2% to about 2.0%, or from about 0.2% to about 1.5%, or from about 0.3% to about 1.0%, or from about 0.35% to about 0.75%, or from about 0.4% to about 0.5%, or is about 0.45%, or any suitable combination, sub-combination, range, or sub-range thereof by weight, based on the weight of the composition. In accordance with some embodiments, the amount of beta hydroxy acid present is not more than about 0.40% to about 0.50%.

Thus, any one of or a combination of beta hydroxy acid is present, by weight, based on the total weight of the composition, from about 0.20, 0.30, 0.40, 0.50, 0.60, 0.70, 0.80, 0.90, 1.0, 1.1, 1.2, 1.3, 1.4, 1.5, 1.6, 1.7, 1.8, 1.9 to about 2.0 weight percent, including increments and ranges therein and there between.

Phenylethyl Resorcinol

In accordance with some various embodiments, the composition according to the disclosure may comprise phenylethyl resorcinol.

Phenylethyl resorcinol functions a tyrosinase inhibitor. The phenylethyl resorcinol, when utilized in the composition according to the present disclosure effectively whiten skin and reduce skin tone unevenness.

Phenylethyl resorcinol has not shown adverse effects in basic toxicological tests, including acute oral toxicity, mutagenicity, skin irritation, skin sensitization, and phototoxicity.

In accordance with the various embodiments, the amount of phenylethyl resorcinol present in the composition is from about 0.2% to about 2.0%, or from about 0.2% to about 1.5%, or from about 0.4% to about 1.0%, or from about 0.6% to about 0.9%, or from about 0.7% to about 0.8%, or from about 0.2% to about 0.8%, is about 0.75%, or any suitable combination, sub-combination, range, or sub-range thereof by weight, based on the weight of the composition. In accordance with some embodiments, the amount of phenylethyl resorcinol present is not more than about 0.2% to about 0.8%.

Thus, phenylethyl resorcinol, when present in the composition, is present, by weight, based on the total weight of the composition, from about 0.20, 0.30, 0.40, 0.50, 0.60, 0.70, 0.80, 0.90, 1.0, 1.1, 1.2, 1.3, 1.4, 1.5, 1.6, 1.7, 1.8, 1.9 to about 2.0 weight percent, including increments and ranges therein and there between.

Solvents

In accordance with the various embodiments, water is present in the composition in a range from about 20% to about 60%, or from about 25% to about 55%, or from about 30% to about 45%, or from about 35% to about 40%, or from about 22% to about 28%, or any suitable combination, sub-combination, range, or sub-range thereof by weight, based on the weight of the composition. One of ordinary skill in the art, however, will appreciate that other ranges are within the scope of the invention. Thus, water is present, by weight, based on the total weight of the composition, from about 20, 21, 22, 23, 24, 25, 26, 27, 28, 29, 31, 31, 32, 33, 34, 35, 36, 37, 38, 39, 40, 41, 42, 43, 44, 45, 46, 47, 48, 49, 50, 51, 52, 53, 54, 55, 56, 57, 58, 59 to about 60 weight percent, including increments and ranges therein and there between.

The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the composition is not limited but is generally not less than 3.5. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

In some embodiments, the composition includes one or more solvents comprising alcohol for solubilizing acid, for example, monoalcohols such as monohydric $C_1$-$C_8$ alcohols such as ethanol, propanol, butanol, isopropanol, isobutanol, and benzyl alcohol, and phenylethyl alcohol. In some embodiments, the alcohol solvent is selected from one or a combination of ethanol and isopropyl alcohol.

In accordance with the various embodiments, the amount of alcohol present in the composition is in the range from about 5% to about 20%, or from about 6% to about 18%, or from about 10% to about 15%, or any suitable combination, sub-combination, range, or sub-range thereof by weight, based on the weight of the composition. One of ordinary skill in the art, however, will appreciate that other ranges are within the scope of the invention.

Thus, any one of or a combination of alcohols may be present, by weight, based on the total weight of the composition, from about 5, 6, 7, 8, 9, 10, 11, 12, 13, 14, 15, 16, 17, 18, 19, to about 20 weight percent, including increments and ranges therein and there between.

Optional Additives

The composition can also comprise one or more additives selected from citric acid, sodium chloride; chelating agents; antimicrobial agents; neutralizing/pH-adjusting agents; vitamins; fragrances; pearlescent agents; odor absorbers; coloring materials; essential oils; fruit extracts; and combinations thereof.

In some embodiments, additives may include actives such as tocopherol. In some embodiments, additives may include one or a combination of antimicrobial agents and their salts, selected from, for example, chlorphenesin, caprylyl glycol, phenoxyethanol, caprylhydroxamic acid, benzoic acid, salicylic acid, benzyl alcohol, phenethyl alcohol, benzalkonium chloride, 4-hydroxyacetophenone, piroctone olamine, hexyl glycerin, ethylhexylglycerin, octylglycerin, benzylglycerin, 3-heptoyl-2,2-propandiol, and 1,2-hexandiol, and pentylene glycol.

In accordance with the various embodiments, the amount of one or more actives and additives, alone or in combination, present in the composition can be present in the composition according to the disclosure in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the composition.

Thus, any one or a combination of actives and additives may be present, by weight, based on the total weight of the composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Use of the Composition: The two-phase composition consists of two distinct phases, an aqueous phase and an oily phase, which are easily emulsified by stirring and which rapidly separate/phase-out at rest. The use of this type of biphasic composition involves pre-application agitation to form an emulsion which is of sufficient quality and stability to allow a uniform application of the two phases to the keratinous tissue sought to be treated.

In some embodiments, the composition is applied to the keratinous tissue at a temperature of about 15° C. to about 30° C., or from about 20° C. to about 25° C.

The composition is suitable for home-use or home application. As such, the composition according to the present invention is applied by a non-professional or is self-applied in a non-clinical environment.

The composition may be applied in any manner, for example, by pasting, spraying, wiping, dispensing, etc. (hereinafter "applying") on the keratinous tissue. This can typically be accomplished with, for example, a spray bottle, an absorbent cotton swab wetted with the concentrated solution, with a solution-wetted sable brush or by gentle wiping with a solution-wetted absorbent fibrous material, such as a gauze square or nonwoven pad, but other solution application techniques that coat the skin with the solution, in a uniform manner, are also feasible.

The composition is applied and allowed to air dry without removal until the user employs their usual cleansing routine. Of course, the composition may optionally be removed after application and some selected interval of time, though the results may not be as desirable. Drying may be promoted by directing a gentle stream of air, warm air, onto the treated area or by other analogous procedures. A single uniform application of the composition to the keratinous tissue is generally sufficient. Additional or multiple applications either before or immediately after the applied solution has dried are normally unnecessary but may be useful in some situations, e.g., in treating keratinous tissue on other parts of the body other than the face or in treating keratinous tissue severely in need of peeling.

EXAMPLES

Inventive and comparative compositions used in the examples were prepared by dissolving salicylic acid in alcohol at room temperature. Once salicylic acid was completely dissolved, phenylethyl resorcinol, was added to the solution, mixed and dissolved at room temperature. Lactic acid was added and mixed well, and all other ingredients were added in any order.

Example 1: Raw Materials

Raw Materials as used herein include isopropyl myristate, salicylic acid, lactic acid, phenylethyl resorcinol, isononyl isononanoate, dicaprylyl carbonate, mineral oil, C13-15 alkane/hemisqualane, squalane, dimethicone, C17-18 branched alkanes. Percentages of each ingredient as may be exemplified in the following examples are shown as amount of active, wherein the raw materials may be present in an amount that is equal to the amount of active, or if the raw material has a concentration of active that is less than 100% then the composition includes the raw material in a greater amount by weight that includes active and a suitable solvent.

Example 2: Inventive Compositions

Representative embodiments of the inventive composition are exemplified herein in Table 1. In the exemplified embodiments, the composition is a biphase, leave-on acid peel that is free of surfactant and includes lactic acid, salicylic acid, phenylethyl resorcinol and high percentage oil.

TABLE 2

| Inventive Composition | | |
|---|---|---|
| INCI (US/UE) | Inventive 1 | Inventive 2 |
| PHENYLETHYL RESORCINOL | 0.75 | 0.75 |
| POTASSIUM HYDROXIDE | 1 | 1 |
| LACTIC ACID | 10 | 5 |
| ALCOHOL DENATURED | 11 | 11 |
| SALICYLIC ACID | 0.45 | 0.25 |
| WATER/AQUA | QS | QS |
| ISOPROPYL MYRISTATE | 50 | 50 |

Example 3: Comparative Composition

An exemplary embodiment of a comparative composition is provided in Table 3 wherein the composition represents a typical Jessner peel that includes 10% lactic acid, phenylethyl resorcinol, and 0.45% salicylic acid in water (no oil).

TABLE 3

| Comparative Composition | |
|---|---|
| INCI (US/UE) | Comparative 1 |
| PHENYLETHYL RESORCINOL | 0.75 |
| POTASSIUM HYDROXIDE | 1 |
| LACTIC ACID | 10 |
| ALCOHOL DENATURED | 11 |
| SALICYLIC ACID | 0.45 |
| WATER/AQUA | 78 |

Example 4

In Vitro Stratum Corneum Comparison of ΔT using differential scanning calorimetry (DSC) to characterize the stability of a protein or other biomolecule directly in its native form. It does this by measuring the heat change associated with the molecule's thermal denaturation when heated at a constant rate.

Studies were conducted with each of the exemplified inventive and comparative compositions, to evaluate effect of the compositions on the stratum corneum. Inventive 1 and Inventive 2 compositions and the Comparative composition together with Jessner peel, glycolic acid alone and isopropyl myristate controls were evaluated on SC samples according to the following procedure. Stratum corneum samples were equilibrated at 75% RH overnight. Inventive and Comparative Compositions and control treatments applied on SC surface (0.1 g/sample) for 15 min in 75% RH. The SC surface was wiped clean and rinsed with DI water. Allow to dry in 75% RH overnight. The DSC profile was measured from 20° C. to 120° C. at 5° C./min. Results are shown in Table 4.

TABLE 4

Measurement of lipid disorganization

| As shown in FIG. 1 | Composition | ΔT |
|---|---|---|
| 70% GA | Glycolic Acid Control | 5.94 ± 0.41 |
| 10% lactic acid, 0.45% salicylic acid in water/IPM | Inventive 1 | 9.39 ± 0.26 |
| 10% lactic acid, 0.45% salicylic acid in water | Comparative 1 | 3.56 ± 0.64 |
| 5% lactic acid, 0.25% salicylic acid in water/IPM | Inventive 2 | 7.46 ± 0.23 |
| 5% lactic acid, 0.25% salicylic acid in water | Jessner Control | 2.68 ± 0.23 |
| IPM | Isopropyl myristate control | 6.40 ± 0.1 |

As shown in the results, with the same level of AHA and BHA, AHA+BHA in isopropyl myristate with water at a ratio of water to oily phases of 1:1, the Inventive compositions outperform each of the Comparative 1 comprising AHA+BHA in in water, and control compositions. The results demonstrate the Inventive Composition provides an unexpectedly improved peel efficacy at the same or lower acid levels.

Example 5: In Vivo Tape Stripping Protein Removed Using a Micro BSC Assay to Characterize the Efficacy of Desquamation Studies were conducted with each of the exemplified inventive and comparative compositions, to evaluate effect of the compositions on live skin tape stripping samples. Inventive 1 and Inventive 2 compositions and the Comparative composition together with Jessner peel, glycolic acid alone and isopropyl myristate controls were evaluated according to the following procedure. Tape strips of skin areas tested with each composition were obtained, with 4 tape strippings per region; Average of 3 regions; Experiment done on single person rinse the forearm with distilled water and dry it for 3 minutes; Wipe with the peel test composition saturated cotton pads on the designated area and dry it for 15 min; Rinse the forearm with the water and dry the moisture by placing a tissue and patting the tissue. Air dry it for 3 min; Perform the tape stripping—(1) put the tape on, (2) place the metal plate on top of the tape, and (3) put weight (2 kg) for 5 seconds.—3 tapes (3 different regions of the skin)/peel test composition×4 tape stripping; Each tape (1.4 cm) was inserted in a 2 mL Eppendorf tube and 500 uL of PBS was added to each tube; Shaking condition (13000 rpm) for 2 hours @ room temperature; Sonication for 20 min in ice water; Micro BCA assay. Results are shown in Table 5.

TABLE 5

Measurement of protein removed

Figure 2:
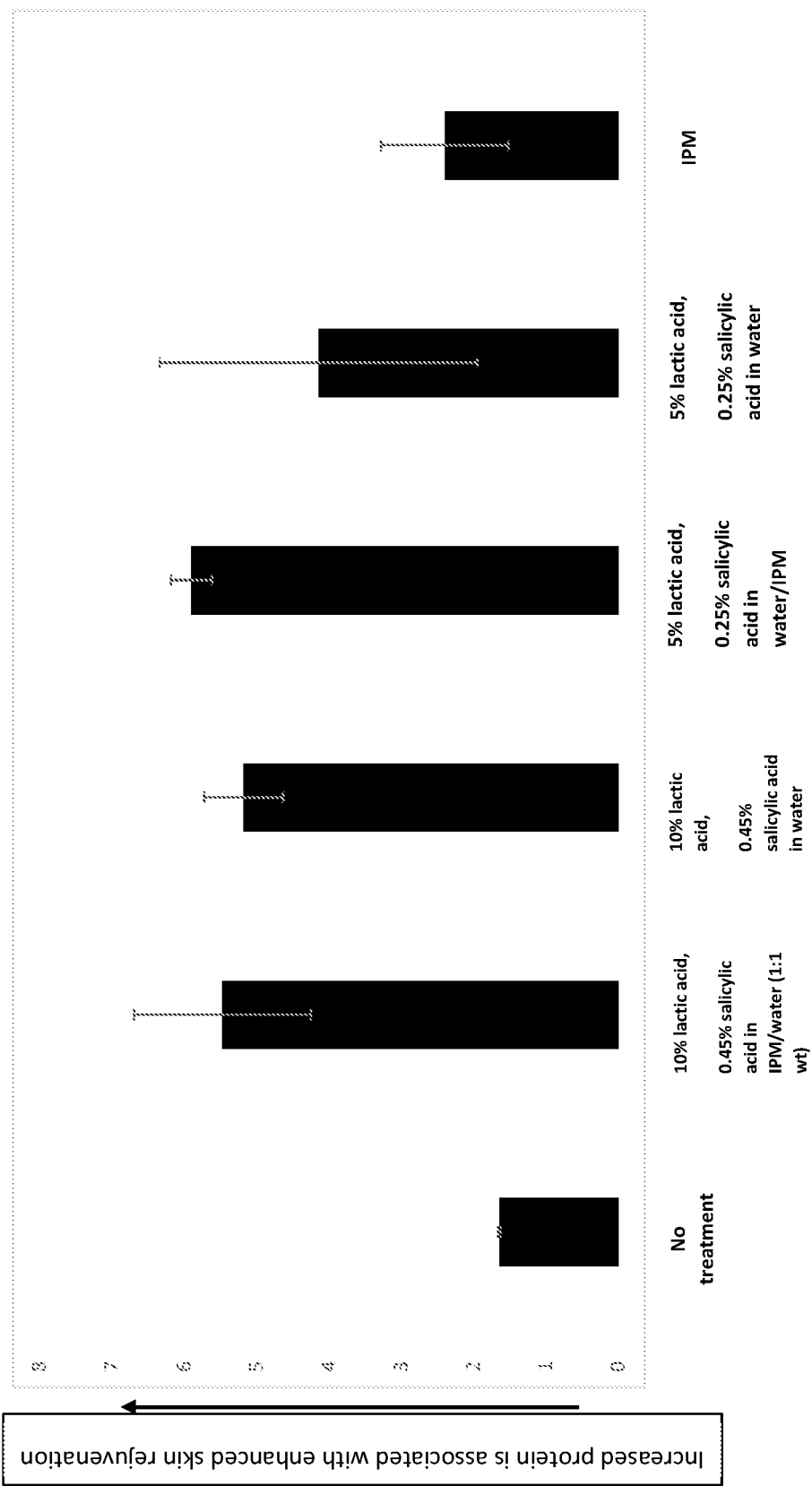
FIG. 2 is a bar graph showing comparative performance results demonstrating extracted protein.

| As shown in FIG. 2 | Composition | Protein Content (μg/cm$^2$) |
|---|---|---|
| 70% GA | Glycolic Acid Control | 1.65 ± 0.02 |
| 10% lactic acid, 0.45% salicylic acid in water/IPM | Inventive 1 | 5.47 ± 1.22 |
| 10% lactic acid, 0.45% salicylic acid in water | Comparative 1 | 5.18 ± 0.55 |
| 5% lactic acid, 0.25% salicylic acid in water/IPM | Inventive 2 | 5.9 ± 0.28 |
| 5% lactic acid, 0.25% salicylic acid in water | Jessner Control | 4.15 ± 2.2 |
| IPM | Isopropyl myristate control | 2.4 ± 0.88 |

As shown in the results with in vivo tape stripping: 5% AHA with BHA mixed oil/water (1:1) demonstrates similar level of efficacy to 10% AHA with BHA in water. The results demonstrate the Inventive Composition provides an unexpectedly improved peel efficacy at the same and at lower acid levels as compared with the comparative composition that lacks oil.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"One or more," as used herein, means at least one, and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "from about 1% to about 10%, or from about 2% to about 8%, or from about 3% to about 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "from about 1% to about 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a certain embodiment, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention is not limited to the particular embodiment disclosed as the best mode contemplated for carrying out this invention, but that the invention will include all embodiments falling within the scope of the appended claims.

We claim:

1. A biphasic skin peel composition, comprising:
   about 4% to about 15% by weight based on the total weight of the composition of at least one alpha hydroxy acid selected from the group consisting of lactic acid, glycolic acid, tartaric acid, mandelic acid, citric acid, ester derivatives thereof, and combinations thereof;
   about 0.2% to about 2.0% by weight based on the total weight of the composition of at least one beta hydroxy acid selected from the group consisting of salicylic acid, beta-hydroxypropionic acid, beta-hydroxybutyric acid, beta-hydroxy beta-methylbutyric acid, carnitine, and combinations thereof;
   about 30% to about 60% by weight based on the total weight of the composition of at least one non-water miscible oil including an oil selected from the group consisting of isopropyl myristate, isononyl isononanoate, dicaprylyl carbonate, and combinations thereof;
   about 0.2% to about 2.0% by weight based on the total weight of the composition of phenylethyl resorcinol;
   about 20% to about 60% by weight based on the total weight of the composition of water; and
   about 5% to about 20% by weight based on the total weight of the composition of alcohol selected from the group consisting of monohydric $C_1$-$C_8$ alcohols, benzyl alcohol, phenylethyl alcohol, and combinations thereof;
   wherein the composition has a pH of at least 3.5;
   wherein the at least one alpha hydroxy acid, the at least one beta hydroxy acid, the phenylethyl resorcinol, the water, and the alcohol are present in a water phase, the at least one non-water miscible oil is present in an oily phase, and the water phase and oil phase are present as two distinct non-emulsified phases,
   wherein the water and oily phases are present in equal amounts (about 1:1), and
   wherein the biphasic skin peel composition has improved peel efficacy at the same or lower acid levels relative to a comparative Jessner peel including additional water in lieu of the at least one non-water miscible oil.

2. The biphasic skin peel composition according to claim 1, wherein the phenylethyl resorcinol is present from about 0.2% to about 0.8% by weight based on the total weight of the composition.

3. The biphasic skin peel composition according to claim 2, wherein the alpha hydroxy acid comprises one or a combination of the lactic acid or the glycolic acid, the beta hydroxy acid comprises the salicylic acid, and the non-water miscible oil is isopropyl myristate.

4. The biphasic skin peel composition according to claim 1, wherein the composition is surfactant free.

5. A biphasic skin peel composition, comprising:
   a. about 4% to about 15% by weight based on the total weight of the composition of at least one alpha hydroxy acid selected from the group consisting of lactic acid, glycolic acid, tartaric acid, mandelic acid, citric acid, ester derivatives thereof, and combinations thereof;
   b. about 0.2% to about 2.0% by weight based on the total weight of the composition of at least one beta hydroxy acid selected from the group consisting of salicylic acid, beta-hydroxypropionic acid, beta-hydroxybutyric acid, beta-hydroxy beta-methylbutyric acid, carnitine, and combinations thereof;
   c. about 30% to about 60% by weight based on the total weight of the composition of at least one non-water miscible oil including an oil selected from the group consisting of isopropyl myristate, isononyl isononanoate, dicaprylyl carbonate, and combinations thereof
   d. about 0.2% to about 2.0% by weight based on the total weight of the composition of phenylethyl resorcinol;
   e. about 20% to about 60% by weight based on the total weight of the composition of water; and
   f. about 5% to about 20% by weight based on the total weight of the composition of alcohol selected from the group consisting of monohydric $C_1$-$C_8$ alcohols, benzyl alcohol, phenylethyl alcohol, and combinations thereof;
   wherein the composition has a pH of at least 3.5,
   wherein the alpha hydroxy acid, beta hydroxy acid, phenylethyl resorcinol, water, and alcohol are present in a water phase, the non-water miscible oil is present in an oily phase, and the water phase and oil phase are present as two distinct non-emulsified phases, and
   wherein the biphasic skin peel composition has improved peel efficacy at the same or lower acid levels relative to a comparative Jessner peel including additional water in lieu of the at least one non-water miscible oil.

6. The biphasic skin peel composition according to claim 5, wherein the at least one alpha hydroxy acid is lactic acid.

7. The biphasic skin peel composition according to claim 5, wherein the composition comprises from about 4% to about 10%, by weight, of the at least one alpha hydroxy acid.

8. The biphasic skin peel composition according to claim 5, wherein the composition comprises about 10.0%, by weight, of the at least one alpha hydroxy acid.

9. The biphasic skin peel composition according to claim 5, wherein the at least one alpha hydroxy acid is lactic acid, glycolic acid, or a combination of lactic acid and glycolic acid.

10. The biphasic skin peel composition according to claim 5, wherein the at least one beta hydroxy acid is salicylic acid.

11. The biphasic skin peel composition according to claim 5, wherein the at least one beta hydroxy acid is salicylic acid, present at about 0.45% by weight based on the total weight of the composition.

12. The biphasic skin peel composition according to claim 5, wherein the at least one non-water miscible oil is free of additional oils.

13. The biphasic skin peel composition according to claim 5, wherein the phenylethyl resorcinol is present from about 0.2% to about 0.8% by weight based on the total weight of the composition.

14. The biphasic skin peel composition according to claim 5, wherein the alcohol is present from about 10% to about 15% by weight based on the total weight of the composition.

15. The biphasic skin peel composition according to claim 5, wherein the at least one alpha hydroxy acid is lactic acid, the at least one beta hydroxy acid is salicylic acid, and the at least one non-water miscible oil is isopropyl myristate.

16. The biphasic skin peel composition according to claim 5, further comprising one or more additives selected from the group consisting of citric acid, sodium chloride, chelating agents, antimicrobial agents, neutralizing/pH-adjusting agents, vitamins, fragrances, pearlescent agents, odor absorbers, coloring materials, essential oils, fruit extracts, and combinations thereof.

17. A biphasic skin peel composition, comprising:
about 8% to about 12% by weight based on the total weight of the composition of lactic acid;
about 0.2% to about 0.75% by weight based on the total weight of the composition of salicylic acid;
about 30% to about 60% by weight based on the total weight of the composition of isopropyl myristate;
about 0.2% to about 0.8% by weight based on the total weight of the composition of phenylethyl resorcinol;
about 20% to about 60% by weight based on the total weight of the composition of water;
about 5% to about 15% by weight based on the total weight of the composition of denatured alcohol, and combinations thereof; and
about 0.1% to about 2% by weight based on the total weight of the composition of a neutralizing/pH-adjusting agent,
wherein the lactic acid, the salicylic acid, the phenylethyl resorcinol, the neutralizing/pH-adjusting agent, the water, and the denatured alcohol are present in a water phase, the isopropyl myristate is present in an oily phase, and the water phase and oil phase are present as two distinct non-emulsified phases, and
wherein the biphasic skin peel composition has improved peel efficacy at the same or lower acid levels relative to a comparative Jessner peel including additional water in lieu of the isopropyl myristate.

18. The biphasic skin peel composition according to claim 17, wherein the composition is surfactant free.

19. The biphasic skin peel composition according to claim 17, wherein the composition is characterized as leave-on, being light-weight, with a pleasing feel upon application, with little to no skin irritation and discomfort.

20. The biphasic skin peel composition according to claim 17, wherein the neutralizing/pH-adjusting agent includes potassium hydroxide.

* * * * *